United States Patent [19]

Feldner et al.

[11] Patent Number: 4,895,969
[45] Date of Patent: Jan. 23, 1990

[54] PROCESS FOR THE PRODUCTION OF ORGANOSILANES

[75] Inventors: Kurt Feldner, Leverkusen; Bruno Degen, Much; Gebhard Wagner, Odenthal; Manfred Schulze, Leichlingen, all of Fed. Rep. of Germany

[73] Assignee: Bayer Aktiengesellschaft, Leverkusen, Fed. Rep. of Germany

[21] Appl. No.: 370,353

[22] Filed: Jun. 22, 1989

[30] Foreign Application Priority Data

Jul. 9, 1988 [DE] Fed. Rep. of Germany ....... 3823308

[51] Int. Cl.$^4$ .............................................. C07F 7/16
[52] U.S. Cl. ................................................... 556/472
[58] Field of Search ......................................... 556/472

[56] References Cited

U.S. PATENT DOCUMENTS

| 2,380,995 | 8/1945 | Reebow | 556/472 |
| 3,536,743 | 10/1970 | Schrader et al. | 556/472 |
| 3,560,545 | 2/1971 | Schrader et al. | 556/472 |
| 4,281,149 | 7/1981 | Shade | 556/472 |
| 4,500,724 | 2/1985 | Ward, III et al. | 556/472 |

FOREIGN PATENT DOCUMENTS

| 0138678 | 4/1985 | European Pat. Off. | 556/472 |
| 0138679 | 4/1985 | European Pat. Off. | 556/472 |
| 0191502 | 8/1986 | European Pat. Off. | 556/472 |
| 0194214 | 9/1986 | European Pat. Off. | 556/472 |
| 0195728 | 9/1986 | European Pat. Off. | 556/472 |
| 0223447 | 5/1987 | European Pat. Off. | 556/472 |
| 3425424 | 2/1985 | Fed. Rep. of Germany | 556/472 |
| 3501085 | 8/1985 | Fed. Rep. of Germany | 556/472 |

Primary Examiner—Paul F. Shaver
Attorney, Agent, or Firm—Sprung Horn Kramer & Woods

[57] ABSTRACT

In the production of an organochlorosilane by reaction of silicon or a silicon alloy with an alkyl or aryl chloride in the presence of a copper catalyst, the improvement which comprises employing the silicon or alloy in atomized form.

3 Claims, No Drawings

PROCESS FOR THE PRODUCTION OF ORGANOSILANES

This invention relates to a new process for the production of organochlorosilanes by reaction of atomized silicon with an alkyl or aryl chloride in the presence of a copper catalyst and promoters. More particularly, the invention relates to a process for the production of methyl chlorosilanes.

The basic process for the production of methyl chlorosilanes comprises the direct reaction of finely divided, ground silicon with methyl chloride in the presence of metallic copper or, more rarely, silver as catalyst. The reaction is known to the expert as "Rochow's synthesis" and is described in US-PS 2,380,995.

A mixture of the following silanes (Me=CH$_3$): Me$_2$SiCl$_2$, Me$_4$Si, Me$_3$SiCl, MeSiCl$_3$, SiCl$_4$, HSiCl$_3$, MeHSiCl$_2$ and Me$_2$HSiCl, is predominantly obtained by this process. In addition to the monomeric methyl chlorosilanes mentioned, higher-boiling compounds, including for example methyl chlorodisilanes, methyl chlorotrisilanes, disiloxanes and silmethylenes, are also formed in relatively small quantities.

The monomeric compounds and, in particular, the dimethyl dichlorosilane are generally used for technical applications. Accordingly, efforts are made to obtain this preferred reaction product with as high a selectivity as possible. A measure of this is inter alia the ratio of MeSiCl$_3$ to Me$_2$SiCl$_2$ (the so-called tri/di ratio) which should be as low as possible.

The production of methyl chlorosilanes by reaction of methyl chloride with silicon in a fluidized-bed reactor is of particular commercial interest, methyl chloride used in excess serving both as the reactant and as the fluidizing medium.

Since the first investigations about 40 years ago, there have been a number of publications describing processes for carrying out the reaction, for improving selectivity and for the production of suitable catalysts/promoter systems. A first comprehensive review can be found, for example, in "Organohalosilanes: Precursors to Silicones", Voorhoeve, Elsevier Publishing Company, Amsterdam/New York/London, 1967.

Recent works have largely concentrated on the specific use of trace elements, so-called promoters, in catalyst systems, cf. for example DE-A-3 425 424, EP-A-138 678, EP-A-138 679, DE-A-3 501 085, EP-A-191 502, EP-A-194 214, EP-A-195 728, EP-A-223 447.

Comparatively few publications relate to silicon and, when they do, they are concerned with purity requirements and with physical characteristic data, such as particle size distribution. For example, US-PS 3,133,109 states that particle sizes of 20 to 200 μm are suitable for the optimal operation of a fluidized bed reactor. In US-PS 4,500,724, silicon smaller than 700 μm is regarded as suitable, the mean particle size being said to be between 20 and 300 μm and preferably between 100 and 150 μm. The limits mentioned above count generally as state of the art and experts know that the particular optimum is closely related to the particular reactor system used.

Now, the present invention relates to a process for the production of organochlorosilanes which is characterized in that silicon which has been produced by atomization or a suitable alloy of silicon which has been produced by atomization is used and is thus brought into a finely divided form in which it may be directly used for the production of organochlorosilanes.

The atomizing of metals is a standard process for the production of metal powders and has long been used, for example, for such metals as copper or its alloys.

In general, metal powders produced in this way are subsequently processed by the techniques commonly used in powder metallurgy to form moldings having special properties; cf. Ullmanns Encycklopädie der technischen Chemie, 4th Edition, Vol. 19, page 566, Verlag Chemie, Weinheim, 1980.

Key factors in the atomizing technique are extremely short solidification and cooling times for the silicon.

Completely surprising and novel is the fact that starting material produced in this way shows considerably higher reaction rate in the synthesis of organochlorosilanes.

For the synthesis of methyl chlorosilanes, the process according to the invention is carried out by reacting atomized silicon having a purity of greater than 98.5% and a particle size of less than 500 μm with methyl chloride in the presence of a mechanically prepared mixture of copper catalyst and promoters. The process according to the invention is preferably carried out in a fluidized bed reactor because by far the most favorable yields of desired product are obtained in such reactors and use may also be made of advantages relating to process technology, including for example high heat transfer.

Another preferred embodiment of the process comprises the reaction of a silicon/copper alloy, which has also been obtained by atomizing, with methyl chloride.

Providing they are used in metallic form, so-called promoter elements may of course also be added beforehand to the alloy to be atomized or may even be mechanically mixed with the atomized silicon/copper alloy.

In the last case, too, a fluidized bed reactor is also preferably used to carry out the reaction.

The silicon used in the process according to the invention has a purity of more than 98.5% Si and preferably of more than 99% Si. Particular importance is attributed to the fact that the Pb content of the silicon should not exceed 10 ppm. Since the preferred embodiment of the present invention in terms of process technology comprises the reaction in a fluidized bed reactor, considerable significance is attributed not only to the chemical properties of the silicon, but also to its physical properties, including for example its particle size distribution. The silicon particles should generally be smaller than 500 μm, the particle size distribution preferably being between 30 and 300 μm for a mean particle size of 100 to 150 μm.

The limits indicated above for the preferred particle size distribution also apply to a suitable atomized silicon/copper alloy.

In the preferred embodiment of the process according to the invention for the production of methyl chlorosilanes, 0.5 to 8 parts and preferably 1 to 3 parts catalyst/promoter mixture are used to 100 parts silicon metal. However, this range may be varied within wide limits because the reaction is normally carried out continuously and not discontinuously in a fluidized bed reactor.

If an atomized alloy is used in accordance with the invention, its composition is selected as follows:
Si: 90 to 99% by weight
Cu: 0.5 to 8% by weight.

Both an atomized alloy and also atomized silicon itself may of course contain the typical impurities known to the expert, such as Fe, Al, Ca, Ti, etc.

According to the invention, suitable promoter elements may be added to the melt to be atomized. Promoter elements are known to the expert and reference is made in this regard to the literature cited herein above where the elements zinc, tin and phosphorus are mentioned in particular.

The process according to the invention is carried out at a temperature in the range from 250° to 350° C. and preferably at a temperature in the range from 280° to 330° C.

It is advisable to carry out the proces under a pressure above atmospheric pressure because the volume/time yield is increased in this way.

An excess pressure of up to 10 bar is advisable, an excess pressure of up to 5 bar being the most appropriate.

Under these conditions, selectivity in regard to the formation of dimethyl dichlorosilane is high. In addition, it is possible under these conditions to establish a reaction rate which can be optimally controlled in terms of process technology.

The gaseous methyl chloride is usually used in a large excess for the reaction because it is continuously passed through the contact mass of silicon metal particles and the catalyst/promoter mixture or the atomized alloy and fluidizes the same.

The expert knows that it is not absolutely essential to use fluidized bed reactors, particularly on a laboratory scale, instead the reactors often used are of the type in which the catalyst mass is vibrated or kept in motion by a helical stirrer during the reaction to avoid local heating and to guarantee safe conduct of the reaction.

As the numerous publications cited above show, attempts have hitherto been made to improve not only the selectivity, but also the yield of dimethyl dichlorosilane through the catalyst/promoter system. However, it was found that the reaction rate also reacts very sensitively to promoters and inhibitors. Thus, the subject of the invention according to DE-OS 3 425 424, page 10, is the considerable increase in the rate of formation of dimethyl dichlorosilane.

All the more suprising was the fact that the method of size reduction of the silicon (atomizing as opposed to grinding) should also play such a key role. This effect is surprising and new.

The process according to the invention may of course also be used for the production of other organochlorosilanes. Any changes necessary to the process parameters are familiar to the expert.

The invention is illustrated by the following Examples.

EXAMPLE 1

All the following experiments were carried out in a stirred-bed reactor of glass, internal diameter 30 mm, which is equipped with a helical stirrer. The quantity of silicon or silicon/copper alloy was always the same and always had the same particle size distribution of 71 to 160 μm. Methyl chloride was passed through the catalyst mass from below via a glass frit under a pressure of 2 bar. The quantity of methyl chloride was kept constant and, in every case, amounted to approximately 1.5 l/h at 2 bar. After heating and initiation of the reaction, a steady test phase was established at 300° C. and the quantity of crude silane mixture formed per unit of time was determined under the conditions thus established. The values shown are always averages from four individual determinations under constant boundary conditions of 2 bar, 1.5 l/h methyl chloride and 300° C.

The catalyst mass consisted of 40 g silicon, 3.2 g copper catalyst and 0.05 g ZnO and was homogenized before use. The same catalyst was used in every case. Sample A and sample B are commercially available silicon powders of different origin prepared in the usual way by grinding. Sample C is a silicon powder prepared by atomizing.

For comparable reaction conditions (2 bar, 1.5 l/h MeCl and 300° C.), the following production rates are obtained in g/h crude silane mixture:

A: 5.7 g/h; B: 5.2 g/h; C: 8.3 g/h which corresponds to an increase in the production rate of approximately 45 or 56% through the use of atomized material.

In order more closely to characterize the silicon powders, the main impurities (% by weight) and also the selectivies (expressed as the ratio of methyl trichlorosilane to dimethyl dichlorosilane (T/D)) obtained in the above-mentioned reactor runs are shown in the following:

|     | A     | B     | C     |
| --- | ----- | ----- | ----- |
| Fe  | 0.43  | 0.30  | 0.52  |
| Al  | 0.32  | 0.19  | 0.38  |
| Ca  | 0.07  | 0.10  | 0.008 |
| T/D | 0.059 | 0.079 | 0.092 |

EXAMPLE 2

An alloy of the following composition prepared by atomizing was reacted in the reactor described in Example 1 under the same conditions (2 bar, 1.5 l/h methyl chloroide, 300° C.):

Fe: 0.34; Al: 0.40; Cu: 5.75; Zn: 0.14 (plus other non-analyzed impurities).

The production rates obtained in two experiments, namely 8.13 g/h and 9.4 g/h, were also clearly above otherwise typical production rates of 5 to 6 g/h.

EXAMPLE 3

Example 3 is intended to show that rapid cooling is important to the production rate.

Under the reaction conditions described above, the sample mentioned in Example 1 under C is compared with a sample D of the same atomized material which has been subjected to a heat treatment before being used in the direct synthesis. To this end, the sample was fused in an ampoule in vacuo, heated for 2 h at 1000° C. and then slowly cooled again over a period of another 6 to 8 h.

The following production rates are obtained under the reaction conditions described above for the reaction with methyl chloride (cf. Example 1):

Sample C (unheated): 8.3 g/h

Sample D (heated): 2.35 g/h.

The composition of the catalyst mass was of course the same.

The example shows a reduction in the production rate for crude silanes to approximately 28% in relation to the original sample C, which is attributable solely to the heat treatment.

It will be appreciated that the instant specification and claims are set forth by way of illustration and not limitation, and that various modifications and changes may be made without departing from the spirit and scope of the present invention.

What is claimed is:

1. In the production of an organochlorosilane by reaction of silicon or a silicon alloy with an alkyl or aryl chloride in the presence of a copper catalyst, the improvement which comprises employing the silicon or alloy in atomized form.

2. The process according to claim 1, wherein the silicon reactant is a Si/Cu alloy.

3. The process according to claim 1, wherein the atomized silicon reactant contains promoter elements.

* * * * *